United States Patent [19]

Rabban

[11] 4,122,844

[45] Oct. 31, 1978

[54] SURGICAL RETRACTOR

[76] Inventor: Philipp Rabban, P.O. Box 390942, Miami Beach, Fla. 33139

[21] Appl. No.: 775,138

[22] Filed: Mar. 7, 1977

[51] Int. Cl.² ............................................. A61B 17/02
[52] U.S. Cl. .................................................. 128/20
[58] Field of Search ............................ 128/20, 13–19, 128/3, 10–12

[56] References Cited

U.S. PATENT DOCUMENTS

| 1,067,572 | 7/1913 | Abbott | 128/12 |
| 1,397,090 | 11/1921 | Dimas | 128/10 |
| 2,670,731 | 3/1954 | Zoll et al. | 128/20 |
| 2,693,795 | 11/1954 | Grieshaber | 128/20 |

Primary Examiner—Robert W. Michell
Assistant Examiner—Henry S. Layton
Attorney, Agent, or Firm—C. Bruce Hamburg

[57] ABSTRACT

A surgical retractor of the invention comprises a shaft, an arm connected to one end of the shaft and a blade connected to the arm. The shaft and the arm lie in the same plane. The blade has a portion extending perpendicularly to the aforementioned plane. The axis of a portion of the shaft including the other end thereof is perpendicular to and laterally offset from the aforementioned portion of the blade. The last mentioned end of the shaft is substantially spaced from the plane of the aforementioned blade portion.

5 Claims, 7 Drawing Figures

U.S. Patent  Oct. 31, 1978  4,122,844
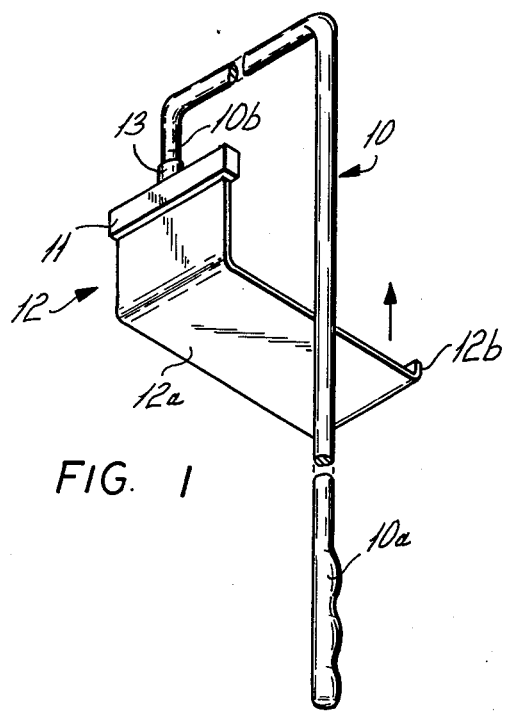
FIG. 1
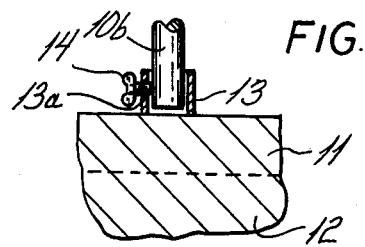
FIG. 2
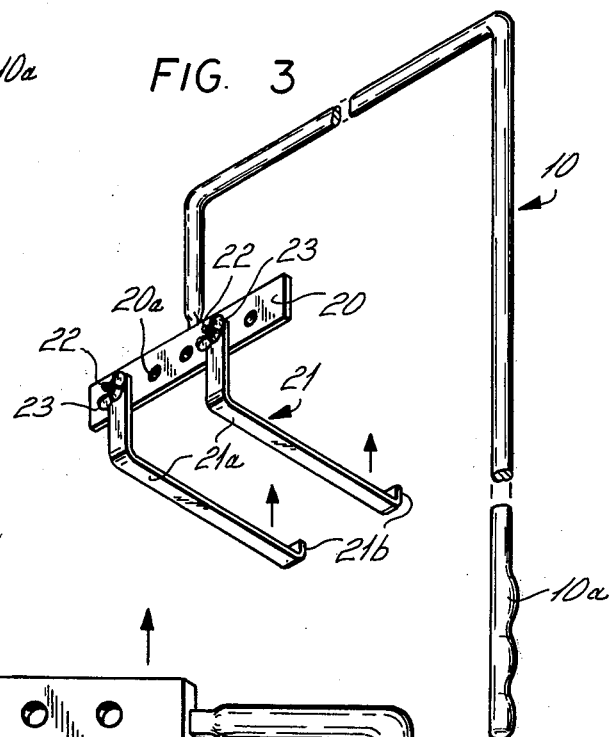
FIG. 3
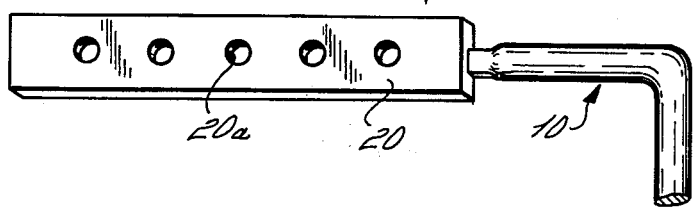
FIG. 4
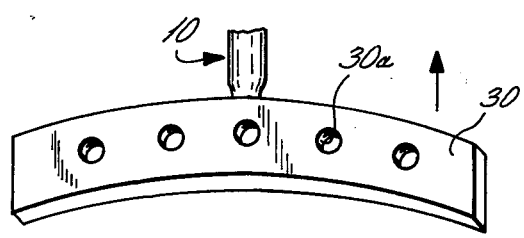
FIG. 6
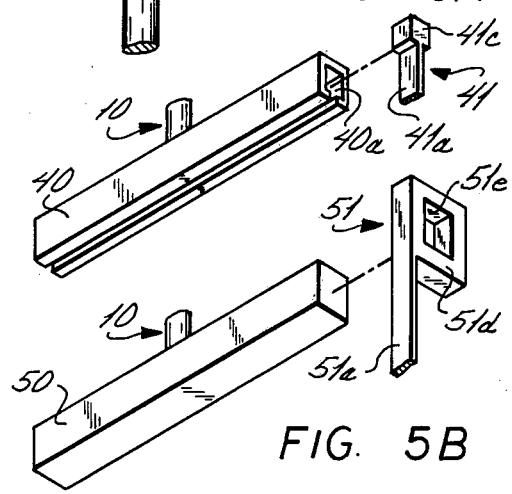
FIG. 5A
FIG. 5B

SURGICAL RETRACTOR

BACKGROUND OF THE INVENTION

This invention relates to an improved surgical retractor primarily for retraction of the ipsilateral, relative to the operator, structures of an incision and, secondarily, for retraction of the cranial and caudal portions of the incision.

Surgical retractors are used to hold a surgical incision open during an operation. Presently, retraction is effected by the pulling of a retractor by an assistant located beside or opposite the operator or by means of a self-retaining retractor. There are numerous disadvantages inherent in the present methods and means for retraction. When the assistant is positioned beside the operator and is pulling a retractor, for the most part the assistant cannot see exactly what he is doing and, moreover, finds the continuous pulling to be very fatiguing. The consequences are inefficiency, i.e., the operation takes longer, hazard, inaccuracy and additional trauma to the patient. Moreover, when the assistant is positioned opposite the operator, in addition to the foregoing disadvantages, the pulling of the retractor is even more fatiguing because the assistant's arm is almost fully extended. Also, particularly when the assistant is positioned alongside the operator, the assistant hampers free movement by the operator. Furthermore, the assistant's arm, in either case, will frequently be resting upon the patient's body and impairing the patient's respiration. The self-retaining retractor, which is typically bilaterally evenly acting, provides retraction on the side at which it is not needed as well as on the side at which it is needed. The retraction is too rigid and traumatic. Moreover, often it must be supplemented with manually effected retraction of one of the aforementioned types.

It is an object of the invention to provide a surgical retractor which avoids the disadvantages of the prior retractors.

Other objects and advantages of the invention will be apparent to one skilled in the art from the following description of the invention.

SUMMARY OF THE INVENTION

According to the present invention, there is provided a surgical retractor which is manipulated by pushing instead of pulling and which, as the result of its unique type of configuration enabling this method of use, avoids all the disadvantages of the prior retractors. The retractor of the invention generally looks like a conventional blade retractor having a shaft to which is connected an arm with one blade or multiple blades being mounted on the arm. However, the shaft, rather than being straight is bent or curved through about 180° or about 90°. In the former case, the shaft is connected to the arm perpendicularly, and, in the latter case, the shaft is connected to the arm endwise, in at least approximate alignment with the arm. In both cases, the shaft and the arm lie in the same plane, the main working portion of the blade or each of the blades is oriented at least approximately perpendicularly to that plane, and the axis of the portion of the shaft remote from the blade and including the other end of the shaft is perpendicular to and laterally offset from the main working portion of each blade. The other end of the shaft, which will generally be in the form of a handle to be grasped by the surgical assistant, is substantially spaced, for example about a foot or more or less from the main working portion of the blade or blades.

In a typical instance, with the plane of the mouth of the incision being horizontal, the retractor is held by the handle at the free end of the shaft so that the shaft and the arm are horizontal and each blade extends vertically downwardly therefrom. Each blade is positioned in the incision and the shaft is pushed to hold the incision open where desired. Pushing of the unique push retractor of the present invention is much less fatiguing than pulling of a conventional retractor. The assistant is leaning toward instead of pulling away from the incision and, consequently, can accurately observe the location of the blade or blades and does not tend to press the retractor shaft against the patient's body. Because the axis of the handle end of the shaft is offset laterally from the main working portion of the blade or blades and the handle end of the shaft is substantially spaced from the plane of the main working portion of the blade or blades, the assistant does not get in the operator's way and the shaft does not impair visibility of the surgical field or the blade or blades. To a great extent, this invention eliminates the need for a second assistant.

BRIEF DESCRIPTION OF THE DRAWINGS

FIG. 1 is an isometric view of a single blade retractor according to the invention;

FIG. 2 is a detail, partly in section, of the retractor of FIG. 1;

FIG. 3 is an isometric view of a multiple blade retractor according to the invention;

FIG. 4 is an isometric view of a portion of a variant of the retractor of FIG. 3;

FIGS. 5A and 5B are respective isometric views of portions of multiple blade retractors according to the invention showing alternative means for mounting the blades on the arms;

FIG. 6 is an isometric view of another variant of the retractor of FIG. 3.

DETAILED DESCRIPTION OF PREFERRED EMBODIMENTS

In each of the figures, the arrows indicate the direction in which the retractor is pushed.

The surgical retractor of FIGS. 1 and 2 comprises a shaft 10 having a handle portion 10a at its free end. The other end of the shaft 10 is releasably connected to an arm 11 to which a retractor blade 12 is permanently connected. The blade has a main working portion 12a formed at the extremity of which is a lip portion 12b. A collar 13 is rigidly connected to the arm 11. The end 10b of the shaft 10 is received in the collar 13 and held in place therein by means of a wing bolt 14 received in a threaded hole in the collar, the end of the wing bolt 14 in the collar 13 locking the shaft end 10b against the inside of the collar 13. As desired, one may loosen the wing bolt 14, rotate the shaft 10 and/or blade 12 180° relative to each other thus, for example, facilitating manipulation of the retractor with the left hand instead of the right.

In order to provide a retractor which is adaptable to a wide variety of surgical procedures, it is desirable to provide means for substituting retractor blades of various shapes and for mounting multiple blades at various spacings. With such spaced blades, the retractor is very well suited for such surgery as of the gall bladder, tumors, the gastrointestinal tract and major blood vessels, as well as pelvic surgery, major orthopedic surgery, and so forth.

In the embodiment of FIG. 3, the arm is in the form of a relatively flat bar 20 provided with a plurality of threaded holes 20a. Retractor blades 21, each having a main working portion 21a and a lip 21b, are fastened to the bar 20 by means of bolts 22, each being screwed into a respective one of the threaded holes 20a and passing through a respective hole provided in each blade 21, and wing nuts 23 screwed onto the bolts 22. It is apparent that the number and spacing of the blades 21 fastened to the bar 20 can be varied and that blades of different sizes and shapes can be substituted. The shaft 10 and handle portion 10a are like that of the embodiment of FIGS. 1 and 2 except that the shaft 10 is permanently rigidly connected to the bar 20. As desired, one may disengage the blades 21 from the bar, change their orientation by 180° and fasten them again to the bar 20 thus, for example, facilitating manipulation of the retractor with the left hand instead of the right.

The retractor of FIG. 6 is exactly like that of FIG. 3 (the blades not being illustrated in FIG. 6) with the exception that the bar 30, provided with threaded holes 30a is curved, which is particularly useful for certain kinds of surgery, such as pelvic surgery.

The retractor of FIG. 4 is exactly like that of FIG. 3 (the blades not being illustrated in FIG. 4) with the exception that the shaft 10 is connected to the end of the bar 20 so that the axis of the shaft 10 at the connection is aligned with instead of at right angles to the long dimension of the bar 20.

The retractors of FIGS. 5A and 5B are designed for infinite adjustability of the blades 41 and 51 along the generally square cross sectioned arms 40 and 50 to which the shaft 10 is connected. The blades 41 and 51 are provided with horizontal portions 41a and 51a as well as vertical main working portions and lips (not illustrated) similar to the embodiment of FIG. 3. A channel 40a is formed in the arm 40 and a broadened portion 41c is formed on the non-working end of the blade 41 for sliding with a snug fit in the channel 40a. Hence, a blade 41 or plurality thereof can be adjusted to any desired positions along the length of the arm 40 and the friction of the snug fit will hold the blades in the selected positions during normal manipulations of the retractor in an operation.

The embodiment of FIG. 5B is similar in principle to that of FIG. 5A. Here, however, the arm is the male member and the blades are the female members. Each blade 51 is provided with a broadened portion 51d provided with a square opening 51e in which the arm 50 is received with a snug fit. As in the embodiment of FIG. 5A, during normal manipulations of the retractor in an operation, the blades 51 will retain the positions to which they have been slid.

While the invention has been particularly described by reference to certain embodiments thereof, it is to be understood that this was intended to illustrate rather than limit the invention and that the scope of the patent, as defined by the hereto appended claims, is intended to encompass all obvious variations and modifications thereof. For example, in FIG. 1, the shaft 10 may be permanently connected to the arm 11.

What I claim is:

1. A hand held surgical retractor comprising a shaft, the shaft having a first portion and a second portion, the second portion being oriented substantially perpendicularly to the first portion, an arm rigidly connected to one end of the second shaft portion and a flat blade rigidly connected to the arm, an end of the first shaft portion being free, a handle being formed at the free end of the first shaft portion, the shaft and the arm lying in the same plane and the blade having a portion extending substantially perpendicularly to said plane and having a free end, a lip formed at said free end and extending away from said handle, the axis of a portion of the shaft including the handle being substantially perpendicular to the plane of said flat blade and laterally offset from said portion of the blade and said end of said first shaft portion being substantially spaced from the plane of said blade portion.

2. A surgical retractor according to claim 1, comprising means for releasably rigidly connecting the arm to the second shaft portion with said portion of the blade at either of two orientations offset from each other by 180°.

3. A surgical retractor according to claim 1, comprising a plurality of blades and means for releasably rigidly connecting the blades to the arm at various positions on the arm.

4. A surgical retractor according to claim 1, in which said second shaft portion includes a portion extending substantially parallel to said first shaft portion all portions of said shaft lying in a common plane.

5. A surgical retractor according to claim 4, in which said portion of said second shaft portion extends from said second shaft toward said handle.

* * * * *